US005536647A

United States Patent [19]
Ceriani et al.

[11] Patent Number: 5,536,647
[45] Date of Patent: Jul. 16, 1996

[54] NUCLEIC ACIDS AND VECTOR ENCODING HMFQ POLYPEPTIDE, TRANSFECTED HOST, FUSION PROTEINS THEREOF, COMPOSITIONS THEREOF AND METHODS OF USE THEREOF

[75] Inventors: Roberto L. Ceriani; Jerry A. Peterson, both of Lafayette; David J. Larocca, San Leandro, all of Calif.

[73] Assignee: Cancer Research Fund of Contra Costa, Walnut Creek, Calif.

[21] Appl. No.: 280,409

[22] Filed: Jul. 25, 1994

Related U.S. Application Data

[60] Continuation of Ser. No. 12,605, Feb. 2, 1993, abandoned, which is a division of Ser. No. 472,136, Jan. 30, 1990, abandoned.

[51] Int. Cl.$^6$ .............................. C12P 21/02; C12N 15/12
[52] U.S. Cl. ................... 435/69.1; 435/69.7; 435/252.3; 435/320.1; 536/23.4; 536/23.5
[58] Field of Search .............................. 435/320.1, 252.3, 435/69.1, 69.7; 536/23.4, 23.5; 530/395, 403

[56] References Cited

PUBLICATIONS

Larocca, D., et al, (1990) Cancer Res, 50, 5925, 5930.
Larocca et al. (1990) Cancer Research, vol. 50, "Cloning and Sequencing of a Complementary DNA Encoding a Mr 70,000 human breast epithelial mucin–associated Antigen," pp. 5925–5930.
Young et al. (1983) Proc. Natl. Acad. Sci., vol. 80, "Efficient Isolation of Genes by Using Antibody Probes", pp. 1194–1198.
J. Sambrook, E. F. Fitsch, and T. Maniatis, "Molecular Cloning a Laboratory Manual, " 2nd ed., Cold Spring Harbor, NY, 1989.
Imam, A. et al. (1984) Cancer Research "Immunohistochemical Study of the Expression of Human Milk Fat Globule Membrane Glyco–protein 70." vol. 44 pp. 2016–2022.
Barrett, J. T. (1983) Textbook of Immunology, C. V. Mosby Co., St. Louis pp. 250–252.
Ceriani et al. (1983) Somatic Cell Genetics vol. 9, No. 4 415–427.
Imam et al. (1981) Biochemical Journal vol. 193, 47–54.
Ceriani et al. (1986) Mechanisms of Cancer Metastasis Horm, Powers, Sloane (eds) pp. 237–257.
Ceriani et al, Potential Therapeutic Implications 235–258 (1986).
Ceriani et al, Immunochemistry in Tumor Diagnosis: 233–263 (1985).
Ceriani et al, Cancer Research 47:532–540 (1987).
Ceriani et al, Cancer Research 48:4664–4672 (1988).
Ceriani et al, Somatic Cell Genetics 9:415–427 (1983).
Ceriani et al, PNAS (USA) 74:582–586 (1987).
Peterson et al, Hybridomma (in press, 1990).
Gendler et al, PNAS (USA) 85:2320–2323 (1988).

Gendler et al, Biological Chemistry 263:12820–12823 (1988).
Siddiqui et al, PNAS (USA) 85:2320–2323 (1988).
Taylor–Papadimitriou et al, Breast Cancer Immunodiagnosis and Immunotherapy, Plenum Publishing Corp., New York, 81 (1990).
Xing et al, Breast Cancer Immunodiagnosis and Immunotherapy, Plenum Publ. Corp., N.Y., 211 (1990).
Abe et al, Cancer Research 49:2834–2839 (1989).
Ceriani et al, PNAS (USA) 79:5420–5424 (1982).
Duwe et al, BBRC 165:1305–1311 (1990).
Imam et al, Biochemistry Journal 193:47–54 (1981).
Imam et al, British Journal of Cancer 3:373–378 (1988).
Heid et al, BBA 2:228–238 (1983).
Imam, et al, British Journal of Cancer 3:373–378 (1988).
Peterhans, et al, Analytical Biochemistry 163:470–475 (1987).
Imam, et al, Biochemical Journal 193:47–54 (1981).
Ceriani, et al, Chapter 16 "Breast Cancer Diagnosis with Human Mammary Epithelial Antigens and the Prospective use of Antibodies Them in Therapy", in Mechanisms of Cancer Metastasis: Potential Therapeutic Implications, pp. 235–257 (1986).
Peterson, Jerry A. et al. "Biochemical and Histological Characterization of Antigens Preferentially expresses on the surface and Cytoplasm of Breast Carcinoma Cells Identified by Monoclonal Antibodies against the Human Milk Fat Globule" Hybridoma. vol. 9 No. 3 (1990).
Xing et al, "Reaction of Antibodies to Human Milk Fat Globule (HMFG) With Synthetic Peptides", Breast Cancer Immunodiagnosis & Immunotherapy (Plenum Press) 1990.
Miyako Abe et al, "Structural Analysis of the DF3 Human Breast Carcinoma–associated Protein", Cancer Research 49, 2834–2839 (1989).
Ceriani et al, "Circulating Human Mammary Epithelial Antigens in Breast Cancer", Proc. Natl. Acad. Sci. pp. 5420–5424 (1982).
Duwe et al, "Human Milk–Fat Globule Membrane Derived Mucin is a Disulfide–Linked Heteromer", Biochemical & Biophysical etc. pp. 1305–1311 (1989).

(List continued on next page.)

Primary Examiner—Charles L. Patterson, Jr.
Attorney, Agent, or Firm—Ratner & Prestia

[57] ABSTRACT

A polypeptide has the antibody binding activity of the 70K dalton HMFG differentiation antigen and is also provided as a fusion protein with a second antigenic polypeptide. An antibody has affinity for the polypeptide of the invention or a functional fragment thereof. in vivo and in vitro methods for therapy, vaccination and detecting the presence of the polypeptide, the antibody, the DNA and RNA of the invention are provided. DNA and RNA sequences encode the polypeptide of the invention or fragments thereof and immunoassay kits comprise the antibodies and/or polypeptides of the invention.

22 Claims, 4 Drawing Sheets

OTHER PUBLICATIONS

Imam et al, "Isolation and Characterization of a Major Glycoprotein from Milk–Fat Globule Membrane of Human Breast Milk", Human Cancer Biology, vol. 193, pp. 47–54 (1981).

Heid et al, "Butyrophilin, An Apical Plasma Membrane–Associated Glycoprotein Characteristic of Lactating Mammary Glands of Diverse Species", Elsevier Biomedical Press, pp. 228–238 (1982).

Peterhans, A., Mecklenburg, M., Meussdoerffer, F., and Mosbach, K. "A Simple Competitive Enzyme–Linked Immunosorbent Assay Using Antigen–β–Galactosidase Fusions", *Analytical Biochemistry* 163:470–475, (1987).

Imam, A., Yoshida, S. O., and Taylor, C. R. "Distinguishing Tumor Cells of Mammary From Extramammary Paget's Disease Using Antibodies to Two Different Glycoproteins From Human Milk–Fat–Globule Membrane", British Journal of Cancer, 58:373–378 (1988).

Imam, A., Laurence, D. J. R. and Neville, A. M. "Isolation And Characterization of A Major Glycoprotein From Milk–Fat–Globule Membrane of Human Breast Milk", *Biochemistry Journal* 193:47–54 (1981).

Ceriani, R. L., Peterson, J. A. and Blank, E. W. "Chapter 16: Breast Cancer Diagnosis With Human Mammary Epithelial Antigens And The Prospective Use of Antibodies Against Them In Therapy" *Mechanism of Cancer* Metastasis: Potential Therapeutic Implications. Honn, Powers, Sloane (editors) pp. 235–257 (1986).

NUCLEIC ACIDS AND VECTOR ENCODING HMFQ POLYPEPTIDE, TRANSFECTED HOST, FUSION PROTEINS THEREOF, COMPOSITIONS THEREOF AND METHODS OF USE THEREOF

This application is a continuation of U.S. application Ser. No. 08/012,605, filed on Feb. 2, 1993, now abandoned, which is a divisional of U.S. application Ser. No. 07/472,136 filed on Jan. 30, 1990, now abandoned.

TECHNICAL FIELD

This invention relates to a polypeptide having the antibody binding specificity of the 70 kDalton HMFG differentiation antigen, a polynucleotide, and a polyribonucleotide encoding it, anti-polypeptide antibodies, methods of detecting the polypeptide and DNA and RNA encoding it, a method of imaging cells expressing the polypeptide, a method of detecting antibody to the polypeptide, in vivo and ex vivo methods of delivering a therapeutic agent to a target cell expressing the polypeptide, a fusion protein of the polypeptide and at least one other polypeptide, labeled polynucleotides and polyribonucleotides encoding the polypeptide and a complementary DNA sequence, method of detecting RNA and DNA by hybridization with labeled probes, a method of vaccination with the polypeptide, and method of treating breast cancer with an anti-sense DNA.

BACKGROUND ART

The human milk fat globule (HMFG) has been used extensively as a source of antigenic material for the preparation of both polyclonal and monoclonal antibodies that have found widespread use in the diagnosis (Ceriani, R. L. et al, Potential Therapeutic Implications, 235–258(1986); Ceriani, R. L. et al, Immunocytochemistry in Tumor Diagnosis, 233–263(1985)) and therapy (Ceriani, R. L. et al, Cancer Res.47:532–540(1987); Ceriani, R. L. et al, Cancer Res.48:4664–4672(1988)) of breast cancer, as well as in the study of the breast epithelial cell surface and the processing of its antigenic components (Ceriani, R. L. et al, Somat. Cell Genet.9:415–427(1983); Ceriani, R. L. et al, Proc.Natl.Acad.Sci.(USA)74:582–586(1977)).

Polyclonal antiserum was originally prepared, that after appropriate absorptions with non-breast tissue was found to identify surface antigens of human mammary epithelial cells (HME-Ags) (Ceriani, R. L. et al, Proc.Natl.Acad.Sci.(USA)74:582–586(1977)). This antiserum (anti-HME) had a high specificity for normal breast epithelial cells and breast carcinomas (Ceriani, R. L. et al, Proc.Natl.Acad.Sci.(USA)74:582–586(1977)). It identified mainly three components of the human milk fat globule which had molecular weights of 150 kDa, 70 kDa, and 46 kDa, respectively.

Monoclonal antibodies were first made against the HMFG in 1980. These antibodies were applied to identify a hitherto unknown component of the breast epithelial cell surface, a large molecular weight mucin-like glycoprotein, that was named non-penetrating glycoprotein (NPGP) (Ceriani, R. L. et al, Somat. Cell Genetics 9:415–427(1983)). This latter component appears to be extremely antigenic in the mouse. The vast majority of monoclonal antibodies prepared against HMFG as well as breast tumors have been found to have specificity against different epitopes of this mucin complex. Less frequently, monoclonal antibodies have been prepared against the 70 kDa and 46 kDa components of the HMFG (Ceriani, R. L. et al, Somat. Cell Genetics 9:415–427(1983); Peterson, J. A. et al, Hybridoma, in press (1990)).

The reason for the high immunogenicity of NPGP has recently been elucidated by the characterization of cDNA clones selected from a lambdagt11 breast cell library using both polyclonal and monoclonal antibodies against the mucin (Gendler, S. J. et al, Proc.Natl.Acad.Sci.85:2320–2323(1988); Gendler, S. et al, Biological Chemistry 263:12820–12823(1988)).

These cDNA clones consist of large arrays of highly conserved 60 bp tandem repeats (Gendler, S. J. et al, Proc.Natl.Acad.Sci.85:2320–2323(1988); Siddiqui, J. et al, Proc.Natl.Acad.Sci.85:2320–2323(1988)). The resulting 20 amino acid repeat contains epitopes for several anti-mucin antibodies (Taylor-Papadimitriou et al, Breast Cancer Immunodiagnosis and Immunotherapy Plenum Publishing Corp. New York, in press (1989); Xing, P. X. et al, Breast Cancer Immunodiagnosis and Immunotherapy, Plenum Publishing Corp. New York, in press (1989)).

The repeat is apparently unstable at the genomic level. This may account for the observed polymorphism seen at the gene, RNA and protein levels for this high molecular weight mucin (Siddiqui, J. et al, Proc.Natl.Acad.Sci.85:2320–2323(1988); Gendler, S. et al, Biological Chemistry 263:12820–12823(1988)). An initial report on cDNA cloning of the mucin product suggested that the core protein had a molecular weight of about 68 kDa (Gendler, S. J. et al, Proc.Natl.Acad.Sci.85:2320–2323(1988)). However, the mRNA was found to be large enough to code for proteins from about 170 kDa to 230 kDa (Gendler, S. J. et al, Proc.Natl.Acad.Sci.85:2320–2323(1988); Siddiqui, J. et al, Proc.Natl.Acad.85:2320–2323(1988)); Gendler, S. et al, Biological Chemistry 263:12820–12823(1988)). More recently, using milder deglycosylation methods, a core protein was identified having a molecular weight of about 200 kDa (Abe, M. et al, Cancer Res.49:2834–2839(1989)).

Attention has also been devoted to the study and use of the NPGP mucin complex, largely as a result of its high immunogenicity. Thus, a large number of monoclonal antibodies were prepared against it. However, the smaller components of HMFG also appear to be important molecules on the surface of breast epithelial cells. They have a breast specificity as demonstrated by the anti-HME antibodies (Ceriani, R. L. et al, Proc.Natl.Acad.Sci.USA74:582–586(1977)).

The 46 kDa and 70 kDa HME antigens are found in serum of breast cancer patients and thus can be used as markers for breast cancer in serum assays (Ceriani, R. L. Proc.Natl.Acad.Sci.USA79:5420–5424(1982)). In addition, the 70 kDa component has been found to co-purify with the intact mucin complex and has been reported to be associated with the NPGP mucin complex by means of disulfide bonds, making it a possible linker protein of this surface mucin complex (Duwe, A. K. et al, Biochem.Biophys.Res.Comm.165:1305–1311(1990)).

Further evidence supporting the importance of the about 70 kDalton component of the surface of breast epithelial cells comes from the work of Imam et al, (Imam A. et al, Biochem.J. 193:47–54(1981)). Imam, et al, have purified a 70 kDalton glycoprotein from HMFG membranes that they have termed epithelial membrane glycoprotein (EMGP-70). They have prepared polyclonal antibodies against it and found that the antisera identifies this component on the apical surface of luminal epithelial cells of all ducts and lobules of the mammary gland. It is also present on normal apocrine but not eccrine sweat glands coils and ducts of skin. This antisera also binds to breast carcinomas and has been used to suggest the breast epithelial origin of both mammary and extra-mammary Paget's disease (Imam A. et al, Br.J.Cancer 3:373–378(1988)).

Imam et al (1988), supra, also prepared polyclonal antibodies against a major component of the HMFG that had a molecular weight of 155 kDaltons and found that antisera bound also to the apical surface of lobules and terminal ducts, but not larger ducts of mammary gland. The latter also did not bind to apical surface of normal apocrine and eccrine sweat gland coils and ducts, or sebaceous glands in skin. The MFGM-gp155 did become localized in Paget's disease and breast disease but not in cases of extramammary disease (Imam A. et al, Br.J.Cancer 3:373–378(1988)).

Other authors (Heid, H. W. et al, Biochem.Biophys.Acta 2:228–238(1983)) have characterized a 70 kDalton glycoprotein component from HMFG that they have termed butyrophilin. It is also present on the apical plasma membrane of lactating mammary gland of human breast (Heid, H. W. et al, Biochem.Biophys.Acta 2:228–238(1983)). Heid et al found that two predominant polypeptides in diverse species having molecular weights of 155 kDaltons and 67 kdaltons. The 155 kDalton component was identified by Heid et al as xanthine oxidase and the 67 kDalton component was termed butyrophilin (Heid, H. W. et al, Biochem.Biophys.Acta 2:228–238(1983)). The 67 kDalton molecule is said to be attached to the inner face of the membrane (Heid, H. W. et al, Biochem.Biophys.Acta 2:228–238(1983)).

However, up to the present time the sequences of the different molecular weight polypeptide components or the DNAs and RNAs encoding them are not known. Nor have antibodies been prepared to the recombinant polypeptide sequences containing the epitopes responsible for normal and cancerous breast epithelial cell specificities.

DISCLOSURE OF THE INVENTION

This invention relates to a polypeptide having the antibody binding specificity of the about 70 kDa HMFG differentiation antigen.

This invention also relates to a fusion protein, comprising a polypeptide having the antibody binding specificity of the about 70 kDalton HMFG differentiation antigen; and;

a second antigenic polypeptide bound thereto.

Still part of this invention is an antibody having specificity for a polypeptide having the antibody binding activity of the about 70 kDalton HMFG differentiation antigen or a functional fragment thereof.

Also provided herein is a method of detecting the presence of a polypeptide having the antibody binding activity of the about 70 kDalton HMFG differentiation antigen or a functional fragment thereof in a biological sample, comprising providing a biological sample suspected of comprising the polypeptide;

adding thereto a polypeptide binding effective amount of an antibody having specificity for a polypeptide having the antibody binding specificity of the about 70 kDalton HMFG differentiation antigen or a functional fragment thereof under conditions effective to form an antibody-polypeptide complex; and determining the presence of any complex formed therebetween.

Also part of this invention is a method of determining the presence of epithelial cells in a biological sample, which comprises providing a biological sample suspected of comprising cells of epithelial origin carrying a polypeptide having the antibody binding activity of the about 70 kDalton HMFG differentiation antigen or a functional fragment thereof;

adding thereto a polypeptide binding effective amount of an antibody having specificity for the polypeptide described above, under conditions effective to form an antibody-cell polypeptide complex; and determining the presence of any complex formed therebetween.

Also provided herein is an in vivo method of imaging cells expressing a polypeptide having the antibody binding specificity of the about 70 kDalton HMFG differentiation antigen in a subject, the method comprising administering to a subject a polypeptide binding effective amount of an antibody having specificity for a polypeptide having the antibody binding specificity of the about 70 kDalton HMFG differentiation antigen or a functional fragment thereof under conditions effective to deliver it to an area of the subject's body suspected of having cells expressing the polypeptide or a functional fragment thereof to form an antibody-cell polypeptide complex;

administering to the subject a detectable label capable of binding to the antibody at a site other than the binding site for the polypeptide; and detecting the presence of label in the subject's body associated with any complex formed.

Also part of this invention is a in vivo method of vaccinating a subject with a polypeptide having the binding specificity of the about 70 kDalton HMFG differentiation antigen or a functional fragment thereof, the method comprising administering to a subject a polypeptide having the antibody binding specificity of the about 70 kDalton HMFG differentiation antigen or a functional fragment thereof in an amount and under conditions effective to vaccinate the subject against the polypeptide, functional fragments thereof or cells carrying the polypeptide or functional fragments thereof.

Yet another method is provided herein for detecting the presence of an antibody having specificity for the about 70 kDalton HMFG differentiation antigen in a biological sample, which comprises providing a sample suspected of comprising the antibody;

adding thereto an antibody binding effective amount of a polypeptide having the antibody binding specificity of the about 70 kDalton HMFG differentiation antigen or a functional fragment thereof under conditions effective to form an antibody-polypeptide complex; and determining the presence of any complex formed therebetween.

This invention also relates to a method of detecting the presence of an antibody having specificity for the about 70 kDalton HMFG differentiation antigen in a biological sample, comprising providing a sample suspected of comprising the antibody;

adding thereto an antibody binding effective amount of the fusion protein of this invention under conditions effective to form an antibody-fusion protein complex;

adding thereto a second polypeptide binding effective amount of an anti-second polypeptide antibody under conditions effective to form an antibody-fusion protein-antibody complex; and determining the presence of any antibody-fusion protein-antibody complex formed therebetween.

Also provided herein is an in vivo method of delivering a therapeutic agent to target cells expressing a polypeptide having the antibody binding specificity of the about 70 kDalton HMFG differentiation antigen or a functional fragment thereof in a patient, the method, comprising binding a therapeutic agent to an antibody having specificity for a polypeptide having the antibody binding specificity of the about 70 kDalton HMFG differentiation antigen or a functional fragment thereof at a site other than the polypeptide binding site; and administering to a subject suspected of carrying target cells a therapeutically effective amount of the antibody-bound therapeutic agent under conditions effective for reaching the cells' environment; and allowing for the antibody carrying the therapeutic agent to bind to the cells' polypeptide.

Still part of this invention is an ex vivo method of delivering a therapeutic agent to target cells expressing a polypeptide having the antibody binding specificity of the about 70 kDalton HMFG differentiation antigen or a functional fragment thereof, comprising obtaining a biological sample suspected of comprising target cells from a subject;

binding a therapeutic agent to an antibody having specificity for a polypeptide having the antibody binding specificity of the about 70 kDalton HMFG differentiation antigen or functional fragment thereof at a site other than the polypeptide binding site;

adding the antibody-bound therapeutic agent to the sample under conditions effective to promote the formation of an antibody-cell polypeptide complex; and returning the sample to the subject.

This invention also relates to a polynucleotide encoding a polypeptide having the antibody binding specificity of the about 70 kDalton HMFG differentiation antigen or fragments thereof.

Also provided herein is a polyribonucleotide encoding a polypeptide having the antibody binding specificity of the about 70 kDalton HMFG differentiation antigen or fragments thereof.

Still part of this invention are a polynucleotide and a polyribonucleotide encoding the fusion protein of the invention or antibody binding functional fragments thereof.

This invention also relates to a DNA sequence which is complementary to a polynucleotide encoding a polypeptide having the antibody binding specificity of the about 70 kDalton HMFG differentiation antigen or functional fragments thereof.

This invention also relates to a method of detecting the presence of a polynucleotide sequence encoding a polypeptide having the antibody binding activity of the about 70 kDalton HMFG differentiation antigen or fragments thereof in a sample, the method comprising providing a sample suspected of comprising the polynucleotide;

melting double stranded polynucleotide present in the sample;

adding thereto a hybridization effective amount of a DNA sequence which is complementary to the polynucleotide encoding a polypeptide having the antibody binding activity of the about 70 kDalton HMFG differentiation antigen or a fragment thereof in labeled form under conditions effective to hybridize any polynucleotide present in the sample having a complementary sequence thereto of at least 15 bases; and detecting the presence of the DNA-complementary polynucleotide hybrid.

Also provided by this invention is a method of detecting the presence of an RNA sequence encoding a polypeptide having the antibody binding specificity of the about 70 kDalton HMFG differentiation antigen or a fragment thereof in a sample, comprising providing a sample suspected of comprising the RNA;

adding thereto a hybridization effective amount of a polynucleotide encoding a polypeptide having the antibody binding specificity of the about 70 kDalton HMFG differentiation antigen or fragment thereof in labeled form under conditions effective to hybridize any RNA present in the sample having a complementary sequence of at least 15 bases thereto; and detecting the presence of the polynucleotide-RNA hybrid.

Also encompassed by this invention is a method of detecting the presence of an RNA sequence encoding a polypeptide having the antibody binding specificity of the about 70 kDalton HMFG differentiation antigen or a fragment thereof in a sample, comprising providing a sample suspected of comprising the RNA;

adding thereto a hybridization effective amount of a polyribonucleotide sequence complementary to that of a polyribonucleotide encoding a polypeptide having the antibody binding specificity of the about 70 kDalton HMFG differentiation antigen or fragment thereof in labeled form under conditions effective to hybridize any RNA having a complementary sequence thereto of at least about 15 bases; and detecting the presence of the complementary polyribonucleotide-RNA hybrid.

Also provided herein is a method of detecting the presence of a DNA sequence encoding a polypeptide having the antibody binding specificity of the about 70 kDalton HMFG differentiation antigen or a fragment thereof in a sample, comprising providing a sample suspected of comprising the DNA;

melting double stranded polynucleotides in the sample;

adding thereto a hybridization effective amount of an RNA sequence encoding a polypeptide having the antibody binding specificity of the about 70 kDalton HMFG differentiation antigen or a fragment thereof in labeled form under conditions effective to hybridize any DNA present in the sample having a complementary sequence thereto of at least 15 bases; and detecting the presence of the DNA-RNA hybrid in the sample.

Still part of this invention is a DNA segment comprising an anti-sense sequence to a polynucleotide encoding a polypeptide having the antibody binding specificity of the about 70 kDalton HMFG differentiation antigen or a functional fragment thereof of about 15 to 2,000 bases.

Moreover, also provided is a method of treating breast cancer in a subject in need of such treatment, the method comprising administering to the subject a composition comprising a therapeutically effective amount of the anti-sense DNA described above.

This invention also relates to an immunoassay kit comprising, in separate containers a monoclonal antibody having specificity for a polypeptide provided with the antibody binding specificity of the about 70 kDalton HMFG differentiation antigen or a functional fragment thereof; and anti-antibody immunoglobulin.

Still part of this invention is an antibody detecting kit comprising, in separate containers a polypeptide provided with the antibody binding specificity of the about 70 kDalton HMFG differentiation antigen, or a functional fragment thereof; and anti-antibody immunoglobulin.

A fusion protein kit is also provided herein which comprises, in separate containers a fusion protein comprising a polypeptide having the binding specificity of the about 70 kDalton HMFG differentiation antigen or fragments thereof and a second antigenic polypeptide or fragments thereof which is bound thereto;

an anti-second polypeptide polyclonal or monoclonal antibody; and anti-antibody immunoglobulin.

Also encompassed by this invention is an anti-breast cancer therapeutic kit comprising, in separate containers a monoclonal antibody having specificity for a polypeptide provided with the antibody binding specificity of the about 70 kDaltons HMFG differentiation antigen; and an anti-cancer therapeutic agent selected from the group consisting of immunotoxins and radionucleides.

A more complete appreciation of the invention and many of the intended advantages thereof will be readily perceived as the same becomes better understood by reference to the following detailed description when considered in connection with the accompanying figures.

Other objects, advantages and features of the present invention will become apparent to those skilled in the art from the following discussion.

BEST MODE FOR CARRYING OUT THE INVENTION

This invention arose from a desire by the inventors to improve on prior art technology useful for the early detection, diagnosis, and treatment of breast cancer.

This work relies on the isolation of a cDNA clone (BA 70.1) that encodes a portion of an about 70 kDalton polypeptide component of the HMFG system and monoclonal antibodies that bind the about 70 kDalton component of the HMFG system. These monoclonal antibodies (Mc13 and McR2) have specificity for, and bind to the BA 70.1 cDNA encoded portion of a fusion protein also containing β-galactosidase and made from the BA 70.1 lambda/gtll clone. The sequence of this cDNA (BA 70.1) has only one uninterrupted open reading frame (ORF). The deduced amino acid sequence of this ORF, moreover, shows no extended identity to any sequence contained in the swiss-pro data base nor to the published sequence for a cloned mucin component (NPGP) of the HMFG system (Gendler, S. J. et al, Proc.Natl.Acad.Sci.85:2320–2323(1988); Siddiqui, J. et al, Proc.Natl.Acad.Sci.85:2320–2323(1988)).

In addition, the nucleotide sequence has no extended homology to any nucleotide sequence found in GenBank, and only limited identity with the (PEM) mucin sequence (about 13/14 base pairs) (Gendler, S. et al, Biological Chemistry 263:12820–12823(1988); Taylor-Papadimitriou et al, in Breast Cancer Immunodiagnosis and Immunotherapy, Ceriani, R. L., ed., Plenum Publishing Corp., N.Y. (1989)). This short oligonucleotide sequence is found in the reported 3' region of the PEM gene. The overall sequence of the BA 70.1 cDNA is therefore not related to the mucin structural gene.

The analysis of the BA 70.1 genomic DNA and the size and relative abundance of BA 70.1 RNA found in breast and non-breast cell lines further supports the fact that the cloned DNA sequence comprises a novel gene that is distinct from the cloned mucin component of the HMFG system. Single copy BA 70.1 gene DNA was observed in several different cell lines. This single copy DNA has EcoR1, BamH1, and HindIII restriction fragment polymorphism, among several breast cell lines. In contrast, the known mucin gene has been shown to have a restriction digestion pattern distinct from that observed herein for BA 70.1 with the same restriction enzymes.

Moreover, northern blot analysis revealed the presence of a single BA 70.1 DNA-specific RNA of about 1.8 kilobase that is highly expressed in 6 out of 9 breast lines and cell lines of some other carcinomas, relative to a low level observed in the Raji lymphoid cells. This is in contrast to two higher molecular weight RNAs (6.4 and 4.7 kilobases) observed when the mucin clone was used as a probe (Gendler, S. J. et al, Proc.Natl.Acad.Sci.85:2320–2323(1988); Siddiqui, J. et al, Proc.Natl.Acad.Sci.85:2320–2323(1988)). The mucin RNAs have been shown to be polymorphic, while the BA 70.1 RNAs are not.

The single stranded RNA probe provided herein is complementary to the ORF found in the cDNA insert. This indicates that this ORF represents the sense strand of the BA 70.1 gene. The significance of the lower molecular weight of the second BA 70.1 specific RNA (0.65 kbase) in all lines tested is, however, unclear. The small size and lack of breast specificity suggests it does not code for the about 70 kDalton HMFG component.

The BA 70.1 β-galactosidase fusion protein expressed by the lambda/gtll clone is useful for assaying the presence of the about 70 kDalton HMFG polypeptide component or fragments thereof in serum obtained from breast cancer patients. This fusion protein is also useful as an immunogen for generating second generation monoclonal and polyclonal antibodies. These antibodies can be used, among other applications, to further study the tissue distribution of this antigen and how it relates to the synthesis of its messenger RNAs, to provide improved immunoassays, and to purify and characterize the about 70 kDaltons antigen polypeptide.

Two monoclonal antibodies prepared that identify the about 70 kDalton component, in fact identify a doublet. This is the case for both Mc13 and McR2 monoclonal antibodies. The Mc13 monoclonal antibody, however, also identifies a 150 kDalton component suggesting a relationship between the 70 and 150 kDalton components, at least with respect to the identified epitopes. These two monoclonal antibodies can detect the respective epitopes on this molecule by radioimmunobinding assays on HMFG membranes and on breast carcinoma membrane material. However, neither will stain normal or cancerous tissues by immunohistology to any significant extent. This lack of histologically staining ability precludes the determination of the true tissue specificity of the about 70 kDalton antigenic polypeptide with these monoclonal antibodies.

Northern blots using the cDNA clone in the present work clearly show that the mRNA for this antigen is present in 6 out of 9 breast carcinoma cell lines, and in several other carcinoma cell lines. The RNA for the antigen is, however, present at much lower levels in a lymphoid cell line. This shows epithelial specificity of the about 70 kDalton antigenic component. This, however, does not imply that certain epitopes of the molecule can not have greater breast specificity. Moreover, since it is known that there is often a deregulation of expression of many cell antigens associated with malignancy, the expression of this antigen mRNA in non-breast carcinomas does not imply that the antigen is actually expressed nor that the antigen is found in the normal epithilial cells which are counterparts to cells in these epithelial tumors.

Having cloned a portion of the cDNA of this molecule permits the further deduction of the sequence of the encoded polypeptide, the synthesis of recombinant proteins or synthetic peptides from the known amino acid sequence, and the preparation of a new generation of monoclonal antibodies against this polypeptide. Also possible with the preparation of the fusion DNA and fusion protein of the invention is the further preparation of polyclonal and monoclonal antibodies against the fusion protein that can be selected to be of greater breast specificity. The HMFG membrane system, in fact, truly represents a purified portion of the apical surface of the normal breast epithelial cell. The about 70 kDalton component being a major molecular species of the HMFG membrane thus also represents a major and perhaps important component of the apical surface of the normal breast epithelial cell.

The cDNA clones of the about 70 kDalton polypeptide component of the HMFG system allowed the determination of the amino acid sequence of its corresponding polypeptide moiety. These cDNA clones also allow for the preparation of a new generation of monoclonal antibodies that have sufficient specificity for application to breast cancer immunotherapy, sufficient staining ability in immunohistopathology, for histological evaluation of specificity and prognostic and diagnostic ability, and ability to identify the about 70 kDalton HMFG peptide component or functional fragments thereof in the serum of breast cancer patients, for the construction of serum assays for diagnosis of breast cancer, and the screening for early detection of the disease.

This invention thus provides a polypeptide having the antibody binding specificity of the about 70 kDalton HMFG differentiation antigen. In one preferred embodiment the polypeptide is the 70 kDalton HMFG differentiation antigen or an antibody binding functional fragment thereof, and more preferably has the biological activity of the about 70 kDalton HMFG antigen molecule.

In another preferred embodiment the polypeptide has the amino acid sequence shown in Table 2 or an antibody binding functional fragment thereof, preferably of about 5 to 100 amino acids long, and more preferably 15 to 50 amino acids long. Particularly preferred are amino acid sequences which correspond to the specific epitopes which are recognized by anti 70 kDalton HMFG differentiation antigen antibodies.

Also provided herein is a pharmaceutical composition which comprises an antibody binding effective amount of the polypeptide described above; and a pharmaceutically acceptable carrier.

This pharmaceutical composition is intended for animal, including human, administration. Each dose preferably contains about 0.1 to 1000 mg of the polypeptide, and more preferably about 10 to 500 mg. Any pharmaceutically acceptable carrier can be utilized for the preparation of the composition. Examples of suitable carriers and other additives are flavorings, preservatives, colorants, salt solutions such as saline, oils or solids, among others. However, any liquid or solid carrier which does not hydrolyze the polypeptide is suitable. The pharmaceutical composition as well as the polypeptide itself are best kept under refrigeration and/or frozen. The polypeptide and the pharmaceutical composition may be vacuumed dried and packaged in a sterile container for transportation to their destination. The composition may comprise about 0.01–99.99% of the polypeptide, the remainder being the carrier.

Also provided herein is a fusion protein which comprises the polypeptide described above; and a second antigenic polypeptide or an antibody binding functional fragment thereof which is bound to the polypeptide of the invention.

Typically, the fusion protein may be composed of an antibody binding functional fragment of the polypeptide of the invention bound to an antibody binding functional fragment of the second antigenic polypeptide which are about 10 to 700 amino acids long and 10 to 1100 amino acids long, and preferably about 15 to 50 amino acids long and 200 to 400 amino acids long, respectively. However, other sizes of the polypeptides, either larger or smaller, can be utilized as long as their antibody binding capability is preserved.

As a second antigenic polypeptide any polypeptide is suitable as long as it acts as an antigen to ellicit the formation of antibodies by a mammal as is known in the art. The second antigenic polypeptide may be chosen in addition because it possesses some other property which is of use for the identification and/or use of the fusion protein. By means of example the second antigenic polypeptide may be a protein such as β-galactosidase or a functional fragment thereof. However, any other second antigenic polypeptide may be utilized as long as antibodies to it can be raised.

The polypeptide of the invention and the fusion protein can be prepared by methods known in the art. By means of example, the polypeptide may be prepared synthetically or it may be produced by the expression of a DNA fragment encoding it which can be cloned into a vector and inserted into a host capable of expression. The fusion protein may be prepared by providing a recombinant DNA containing sequences which encode the amino acid sequences of the two polypeptides. This DNA may be cloned into a vector and expressed in a host.

Also part of this invention is an antibody having specificity for a polypeptide having the antibody binding specificity of the about 70 kDalton HMFG differentiation antigen.

Methods for raising antibodies are known in the art and need not be described herein. Particularly preferred are antibodies which are monoclonal antibodies. Methods of preparing monoclonal antibodies against a specific polypeptide are also known in the art and need not be described in detail herein.

The antibodies raised against the biologically pure polypeptide or fragments thereof have increased affinity and/or specificity for the polypeptide. Typically, the affinity may be about $10^{-8}$ to $10^{-5}$, and in some cases greater than $10^{-8}$.

In a particularly preferred embodiment of the invention the antibody also has affinity for the about 150 kDalton differentiation antigen of the HMFG system. Still another preferred embodiment is that wherein the antibody of the invention is the Fab fragment thereof with its binding capacity preserved.

Also provided herein is a pharmaceutical composition which comprises a polypeptide binding effective amount of an antibody having an affinity of about $10^{-10}$ to $10^{-5}$ for a polypeptide provided with the antibody binding specificity of the about 70 kDalton differentiation antigen of the HMFG system; and a pharmaceutically acceptable carrier.

Typically, the antibody is provided in an amount of about 0.001 to 10,000 mg, and more preferably about 10 to 500 mg. Any pharmaceutically acceptable carrier is suitable as indicated above. Other ingredients may also be contained in the composition such as radionuclides, chemotherapeutic drugs, interferon, toxic agents such as ricin A-chain, abrin A-chain, saline salt solutions, preservatives, flavors, colorants and buffers, among others, as is known in the art. The preparation of the pharmaceutical composition can be undertaken as is known in the art by admixing the polypeptide or the antibody with the pharmaceutically-acceptable carrier in the absence of hydrolyzing conditions, then vacuum dried and packaged in a sterile container or provided as a sterile solution.

Also part of this invention is a method of detecting the presence in a biological sample of a polypeptide having the antibody binding activity of the about 70 kDalton HMFG differentiation antigen or a functional fragment thereof, comprising providing a biological sample suspected of comprising the polypeptide;

adding thereto a polypeptide binding effective amount of an antibody having specificity for a polypeptide having the antibody binding specificity of the about 70 kDalton HMFG differentiation antigen under conditions having the antibody binding specificity of the about 70 kDalton HMFG differentiation antigen effective to form an antibody-polypeptide complex; and determining the presence of any complex formed.

This method is suitable for detecting the presence of the polypeptide in biological samples such as animal cells, cell extracts or body fluids. Typically, any body fluids are encompassed herein. Examples are serum, plasma, urine, breast fluid, tissue biopsies, and fine needle aspirates.

The sample may be previously treated, e.g., to avoid interference by metals, non-specific proteins, fats, nucleic acids, and the like.

The biological sample may also be diluted in order that the content of the polypeptide be in a range of about 0.0001 to 10 mg/ml, and more preferably about 0.001 to 0.1 mg/ml. The antibody may be added as known in the art in an amount of about 0.0001 to 1.0 mg/ml of sample, and more preferably about 0.001 to 0.1 mg/ml of sample.

Other conditions for the assay may be as follows. The sample may be homogenized and centrifuged to remove particulate material and fatty material. Detergents may be added to disolve membranes, solubilize fatty material and reduce background. Also added may be carrier proteins such as bovine serum albumin to reduce non-specific binding of the antibodies, and chelators to remove interferring divalent metal ions.

The determination of the presence of any complex formed between the antibody and the polypeptide may be done by a variety of methods known in the art. By means of example will be cited herein the further addition of a labeled anti-antibody immunoglobulin to form a double antibody-polypeptide complex which is labeled. The label may be a radiolabel, a fluorescent label, an enzyme label or biotin to be later detected as a conjugate of avidin, streptavidin or magnetic bead. After this step the amount of label bound to the complex may be assessed by methods known in the art.

Also provided herein is a method of determining the presence in a biological sample of epithelial cells, which comprises providing a biological sample suspected of comprising cells of epithelial origin carrying a polypeptide having the antibody binding activity of the about 70 kDalton HMFG differentiation antigen or a functional fragment thereof;

adding thereto a polypeptide binding effective amount of an antibody having specificity for a polypeptide having the antibody binding specificity of the about 70 kDalton differentiation antigen of the HMFG system under conditions effective to form an antibody-cell polypeptide complex; and determining the presence of any complex formed.

This method is particularly well suited for biological samples such as bone marrow samples. However, it may be practiced with samples of other origin as well. The steps are in general conducted as described above and the determination of the presence of epithelial cells may be done by the identification, either qualitative or quantitative, of any complex formed with the antibody as already described.

The detection may also be undertaken by assaying for the presence of ribonucleic acid (RNA) encoding the about 70 kDalton protein using nucleic acid probes based on sequences such as the one shown in Table 2 and methods known in the art such as PCR (Erlich, H. A., in PCR Technology: Principles and Applications for DNA Amdification, 1989, Stockton Press).

Also provided herein is an in vivo method of imaging cells expressing a polypeptide having the antibody binding specificity of the about 70 kDalton differentiation antigen of the HMFG system in a subject, the method which comprises administering to a subject a polypeptide binding effective amount of an antibody having specificity for a polypeptide with the antibody-binding specificity of the about 70 kDalton HMFG differentiation antigen under conditions effective to deliver it to an area of the subject's body suspected of having cells expressing the polypeptide to form an antibody-cell polypeptide complex;

administering to the subject a detectable label capable of binding to the antibody at a site other than binding site of the polypeptide; and detecting the presence of the label associated with any complex formed in the subject's body.

The antibody may be administered at a concentration of about 0.5 to 50 mg/ml, and more preferably about 5 to 20 mg/ml. A total of about 10 to 50 ml of the antibody composition may be given at any one particular time. The regimen of administration may be a single dose or the antibody may be administered in a continuous manner in order to continuously suppress the presence of polypeptide or functional fragments thereof in the subject's cells. Thus, repeated doses of the antibody composition are also contemplated.

The antibody may be administered in a pharmaceutical composition as described above, or in any other form found suitable. The administration of the antibody may be conducted by the intravenous, intraperitoneal, intracavitary, lymphatic, intratumor and intramusculary routes, among others. Other routes as suitable may also be utilized which will not hydrolyze the peptide links of the antibody.

The administration of a detectable label may be conducted by providing an anti-antibody immunoglobulin or a binding-functional fragment thereof which is labeled and then detecting the amount of label bound to the complex. These technologies are known in the art and need not be further described herein.

Also provided herein is a method of detecting a presence in a biological sample of an antibody having affinity for the about 70 kDalton HMFG differentiation antigen, comprising providing a sample suspected of comprising the antibody;

adding thereto an antibody binding effective amount of a polypeptide having the antibody binding specificity of the about 70 kDalton HMFG differentiation antigen under conditions effective to form an antibody-polypeptide complex; and determining the presence of any complex formed.

The method described above utilizes the polypeptide of the invention in order to detect the presence of antibodies in a mammal generated as a consequence of the presence of such polypeptide in the mammal's body. The sample may be treated as indicated above to eliminate interference of other proteins and/or components of the sample. In the case of blood, serum may be obtained first, and then the serum may be treated as follows.

Normal human or bovine serum may be added, and/or bovine serum albumin (BSA) is used as a blocking agent to reduce non-specific reactivity.

The polypeptide is added to the sample in an amount of about 0.00001 to 1.0 mg/ml of sample, and more preferably about 0.0001 to 0.1 mg/ml of sample. However, other amounts may also be utilized as seen suitable. The amount of antibody in the sample may be controlled by dilution. Optimal ranges of antibody in the sample are about 0.00001 to 0.1 mg/ml, and more preferably about 0.0001 to 0.01 mg/ml. However, other amounts may also be utilized. The steps of this method are practiced as described above, including the determination of the presence of antibody-polypeptide complex. The conditions for the assay are in general those known in the art, such as pH temperature and the like.

Also provided herein is a method of detecting the presence of an antibody having affinity for the about 70 kDalton HMFG differentiation antigen in a sample, the method comprising providing a sample suspected of comprising the antibody;

adding thereto an antibody binding effective amount of a fusion protein comprising a polypeptide having the antibody binding specificity of the about 70 kDalton HMFG differentiation antigen and a second antigenic polypeptide or an antibody binding functional fragment thereof bound to one another under conditions effective to form an antibody-fusion protein complex;

adding thereto a second polypeptide binding effective amount of an anti-second polypeptide antibody under conditions effective to form an antibody-fusion protien-antibody complex; and determining the presence of any antibody-fusion protein-antibody complex form.

As in the case of the previous methods this method is practiced preferably with a monoclonal antibody. The amounts of antibody added to the sample are preferably about 0.00001 to 0.1 mg/ml sample, and more preferably about 0.0001 to 0.01 mg/ml of sample. However, other amounts may also be utilized. As in the previous cases the sample may be pretreated prior to the addition of the fusion protein. One example is the dilution of the sample and the elimination of interfering components. These steps are undertaken as is known in the art and need not be further described herein.

Also provided herein is an in vivo method of vaccinating a subject with a polypeptide having the binding specificity of the about 70 kDalton HMFG differentiation antigen or a functional fragment thereof, comprising administering to a subject to be vaccinated a polypeptide having the antibody binding specificity of the above 70 kdalton HMFG differentiation antigen or a functional fragment thereof in an amount and under conditions effective to vaccinate the subject against the polypeptide, functional fragments thereof or cells carrying the polypeptide or functional fragments thereof. This in vivo method may be utilized to vaccinate a cancer patient against a polypeptide of the described characteristics or cells carrying it. In this manner the patient is induced to raise an immune response against the polypeptide or cells carrying the polypeptide.

The vaccinating polypeptide may be administered to the subject in an amount of about 1 to 100 mg/ml, and more preferably about 2 to 50 mg/ml. Typically, any dose will consist of about 0.1 to 50 ml of the vaccinating polypeptide, and more preferably about 2 to 10 ml. The vaccinating agent may be administrated in a single dose or it may be administered on a continuous basis for periods of up to about 6 months, and sometimes in excess of one year. More prolonged periods of time are also encompassed for vaccination according to this invention.

Also provided herein is an in vivo method of delivering a therapeutic agent to target cells expressing a polypeptide having the antibody binding activity of the about 70 kDalton HMFG differentiation antigen in a patient, comprising binding to a monoclonal antibody having specificity for a polypeptide provided with the antibody-specificity of the about 70 kDalton HMFG differentiation antigen a therapeutic agent at a site other than the polypeptide binding site;

administering to a subject suspected of carrying the target cells a therapeutically effective amount of the antibody-bound therapeutic agent under conditions effective to deliver the agent to the cells' environment; and allowing for the antibody carrying the therapeutic agent to bind to the cells' polypeptide to permit therapeutic agent to exert its effect on the cells.

This in vivo method may be utilized for treating cancer patients that are afflicted with cancer to epithelial cells, e.g., breast cancer.

The therapeutic agent may be any anti-cancer agent known in the art. Examples of therapeutic agents are radionuclides, chemotherapy drugs, toxic agents such as ricin A-chain, abrin A-chain, etc. However, others may also be utilized. The therapeutic agent is bound to the antibody by means known in the art. More specifically, a radionuclide such as $^{131}$I is bound to the antibody by oxidation of amino acids such as tyrosine, or $^{90}$Y attached via a chelator and the conjugate injected intravenously or intraperitoneally into humans carrying human breast tumors, and the growth of the tumor is thus inhibited. (e.g. for mice, Ceriani, et al, Cancer Res. 48:4664–4672(1988)).

The antibody-bound therapeutic agent may be administered to the subject in an amount of about 1 to 100 mg of composition/ml, and more preferably about 2 to 20 mg of composition/mi. Typically, any dose will consist of about 1 to 50 ml of antibody-bound therapeutic agent containing composition and more preferably about 2 to 10 ml. The therapeutic agent may be administered as an antibody-bound agent in a single dose or it may be administered on a continuous bases for periods of up to about 6 months, and sometimes in excess of one year. More prolonged periods of time are also encompassed for treatment herein.

Also provided herein is an ex vivo method of delivering a therapeutic agent to target cells expressing a polypeptide having the antibody binding activity of the about 70 kDalton HMFG differentiation antigen, the method which comprises obtaining from a subject a biological sample suspected of comprising target cells;

binding to a monoclonal antibody having specificity for a polypeptide provided with the antibody binding specificity of the about 70 kDalton HMFG differentiation antigen a therapeutic agent at a site other than the polypeptide binding site;

adding the antibody-bound therapeutic agent to the sample under conditions effective to promote the formation of an antibody-cell polypeptide complex;

allowing the agent to exert its effect on the cells;

and returning the sample to the subject.

The non-conjugated antibody may also be added to the sample in the presence of complement, which causes lysis of the cells, prior to returning the sample to the subject.

In general the steps of this method may be practiced as described above, particularly in terms of the preparation of the biological sample, and binding of the therapeutic agent to the antibody as well as the addition of the antibody-bound therapeutic agent to the sample. With respect to the return of the sample to the subject, this may be done by means known in the art. For example, the already treated sample may be returned to a subject's body in sterile form by the intravenously, intracavitary, intraperitoneal, and intratumor routes. However, other routes known in the art may also be utilized.

Also provided herein is a polynucleotide encoding a polypeptide having the antibody binding specificity of the about 70 kDalton HMFG differentiation antigen of the invention or binding functional fragments thereof. The polynucleotide is provided either as a double stranded DNA or as a single stranded DNA containing the coding strand of the polynucleotide. The fragments of the polynucleotide may be of about 15 to 2,000 bases, and more preferably about 30 to 300 bases.

Also provided herein is a DNA sequence which is complementary to the coding strand of the polynucleotide described above.

Both the double stranded and the single stranded DNAs discussed above are also provided in labeled form. The labeling may be conducted as is known in the art with radioactive atoms such as $^{32}$P, $^{14}$C, $^{3}$H, and the like. However, other radionuclides may also be utilized.

Particularly preferred is a polynucleotide having the DNA sequence shown in Table 2 of this patent or fragments thereof comprising about 9 to 300 bases, and more preferably about 18 to 126 bases. However, fragments of other sizes may also be utilized and are encompassed herein.

Also part of this invention is a polyribonucleotide encoding a polypeptide having the antibody binding specificity of the about 70 kDalton HMFG differentiation antigen or fragments thereof. This is the coding RNA for the polypeptide.

The fragments may be of the size of about 9 to 300 bases long, and more preferably about 18 to 126 bases long. However, other fragment sizes are also encompassed herein.

Still part of this invention is a non-coding strand of a polyribonucleotide having a sequence complementary to that of the polyribonucleotide described above. This polyribonucleotide sequence is capable of hybridization to the coding RNA strand or to the non-coding strand of the corresponding DNA. In a particularly preferred embodiment the polyribonucleotide is provided in labeled form.

Also part of this invention is a polynucleotide encoding a fusion protein comprising a polypeptide having the antibody binding specificity of the about 70 kDalton HMFG differentiation antigen and a second antigenic polypeptide or an antibody binding functional fragment thereof bound to one another.

The polynucleotide may be about 400 to 4,000 bases long, and more preferably about 500 to 1,400 bases long. However, other size polynucleotides are also encompassed herein.

Also provided herein is a polyribonucleotide encoding a fusion protein comprising a polypeptide provided with the antibody binding specificity of the about 70 kDalton HMFG differentiation antigen and a second antigenic polypeptide, or an antibody binding functional fragment thereof bound to one another. Also, a polyribonucleotide is provided which is complementary to the sequence of the RNA encoding the fusion protein.

The polyribonucleotide encoding the fusion protein may be about 400 to 4,000 bases long, and more preferably about 500 to 1,400 bases long. Fragments thereof may be about 9 to 72 long, and more preferably about 12 to 63 bases long.

Still part of this invention is a polynucleotide encoding the fusion protein of the invention or functional fragments thereof about 400 to 4,000 bases long, and more preferably about 500 to 1,800 bases long. The polynucleotide encoding the fusion protein is provided as a double stranded DNA or as a single stranded DNA which encompasses the coding strand of the fusion protein and a second polynucleotide encompassing a sequence corresponding to the non-coding DNA strand or fragments thereof. The latter polynucleotide provided herein is a polynucleotide comprising DNA sequences complementary to the polynucleotide encoding the fusion protein. Both the DNA and RNA sequences encoding the fusion protein may be provided in labeled form. Particularly useful labels are $^{32}$P and others known in the art. The DNAs and RNAs are labeled by methods known in the art.

Also provided herein is the method of detecting the presence in a sample of the polynucleotide sequence encoding a polypeptide having the antibody binding activity of the about 70 kDaltons HMFG differentiation antigen, the method comprises providing a sample suspected of comprising the polynucleotide;

melting double stranded polynucleotide present in the sample;

adding thereto a hybridization effective amount of a DNA sequence which is complementary to the coding strand of a polynucleotide encoding the polypeptide of the invention in labeled form under conditions effective to hybridize any polynucleotide having a complementary sequence of at least 15 bases thereto; and detecting the presence of the DNA-complementary polynucleotide hybrid.

The sample subjected to this method may be a biological sample or it may be a sample generated in the laboratory. If the sample contains cells where the polynucleotide is located, the cells need to be lysed, and optionally the DNA isolated from the remainder materials. This is done by methods known in the art.

The sample may be further diluted and/or prepared for the melting of double stranded polynucleotide sequences present therein. The melting step is conducted as is known in the art. In general, the sample is prepared by lysing the cells in 4M guanidinium isothiocyanate to denature protein and prevent RNAse activity. Extracts are run on a Cesium Chloride density step gradient ultracentrifugation where RNA, DNA and protein are separated according to their relative densities. DNA and RNA are further purified by extraction with organic solvents, and concentrated by precipitation in 70% ethanol. (Sambrook et al, in Molecular Cloning: A Laboratory Manual, Second edition, Cold Spring Harbor Press, N.Y., (1989)). Melting is accomplished by raising the temperature of the sample about 20° C. over the Tm of the DNA, or by raising the pH to above 12.

To the melted DNA is added a hybridization effective amount of labeled DNA complementary to the coding strand of a polynucleotide encoding a polypeptide provided with the antibody binding specificity of the about 70 kDalton HMFG differentiation antigen. The conditions for suitable hybridization of DNA-DNA segments are known in the art. The degree of stringency is determined by the number of complementary sequences desired to be hybridized. In general when more stringent conditions are utilized hybridization will occur with DNA sequences which have a higher degree of complementarity with the probe. Thus, when a low degree of stringency is desired to detect sequences with low complementarity, the conditions may be varied accordingly. In general, the conditions may be as follows.

The conditions can be varied but are generally as follows. The sodium ion concentration is about 1M, the pH about 5–9, the temperature about 65° C. or about 20° C. below the melting temperature of the duplex DNA of the probe sequence and its complementary strand (Britten, R. et al, Methods in Enzymology 29:363(1974); Sambrook et al, supra).

The DNA-complementary polynucleotide labeled hybrid may be detected by methods known in the art. Typically, the double stranded DNA is restricted with enzymes and run on an electrophoresis gel to separate the different size strands. The gel is blotted onto a specially prepared filter, hybridized, and the filter is then exposed to a photographic plate for a period of time effective to obtain a picture thereof. The plate is then developed and the different fragments analyzed.

For a more qualitative detection of the presence of the double stranded labeled hybrid, the unrestricted DNA may be blotted onto a filter, hybridized, exposed to a photographic plate and the plate developed to merely detect the presence of radiolabel.

Also provided herein is a method of detecting the presence of an RNA sequence encoding a polypeptide having the antibody binding activity of the about 70 kDalton HMFG differentiation antigen or a fragment thereof in a sample, comprising providing a sample suspected of comprising the RNA;

adding thereto a hybridization effective amount of the coding strand of a labeled polynucleotide encoding a polypeptide with the antibody binding specificity of the about 70 kDalton HMFG differentiation antigen in single stranded form under conditions effective to hybridize any RNA having a complementary sequence of about at least 15 bases thereto; and detecting the presence of the polynucleotide-RNA hybrid.

In essence, the above method is conducted in a manner similar to the previously described method of detecting the presence of a DNA sequence, with the additional precaution of insuring the lack of degradation of the RNA contained in the sample. In general, in the case of the detection of RNA the following must be additionally done.

The use of RNAse inhibitors and the pretreatment of labware with diethylpyrocarbonate to inactivate any contaminating RNAses. Hybridizations are conducted generally at a higher stringency because RNA:RNA hybrids are more stable than DNA:DNA hybrids. For example, the hybridization may be conducted at 65° C. in 50% formamide. The Tm of DNA duplexes is reduced by about 0.72° C. per 1% formamide added. (See, Sambrook et al, supra; Casey J. and Davidson N., Nucl. Acids Res. 4:1539–1552(1977)).

If the RNA is contained inside the cells, the cells must be lysed to expose the ribonucleic acid. This is done by means known in the art such as detergent lysis, which may be followed by treatment with proteases.

Also provided herein is a method of detecting the presence in a sample of an RNA sequence encoding a polypeptide having the antibody binding activity of the about 70 kDalton HMFG differentiation antigen or a fragment thereof, the method comprising providing a sample suspected of comprising the RNA;

adding thereto a hybridization effective amount of an labeled oligoribonucleotide complementary to at least a portion of a polyribonucleotide sequence encoding a polypeptide provided with the antibody binding specificity of the about 70 kDalton HMFG differentiation antigen under conditions effective to hybridize thereto RNA having a complementary sequence of at least about 15 bases; and detecting the presence of the polyribonucleotide-RNA hybrid.

This method is in general practised in a manner similar to the two previous methods except that in this case precautions must be taken not to permit any degradation of the RNA sequences present in the sample and the probe. The conditions for RNA-RNA hybridization are known in the art. In general, the conditions utilized involve a temperature of about 65° C. and about 50% formamide (mentioned above).

When the RNA is contained inside cells, the cells must be lysed to permit the exposure of the RNA.

Also provided herein is a method of detecting the presence in a sample of a polynucleotide sequence encoding a polypeptide having the antibody binding activity of the about 70 kDalton HMFG differentiation antigen or fragments thereof, the method comprising providing a sample suspected of comprising the polynucleotide;

melting double stranded polynucleotide present in the sample;

adding thereto a hybridization effective amount of a labeled RNA sequence encoding a polypeptide provided with the antibody binding specificity of the about 70 kDalton HMFG differentiation antigen under conditions effective to hybridize thereto any polynucleotide having a complementary sequence thereto of at least about 15 bases; and detecting the presence of the RNA-complementary polynucleotide hybrid.

When the polynucleotide is contained inside the cells the cells must be lysed to expose the DNA.

Also part of this invention is a DNA segment comprising an anti-sense sequence to the coding strand of a polynucleotide encoding a polypeptide having the antibody binding specificity of the about 70 kDalton HMFG differentiation antigen of about 200 to 1,800 nucleotides. More preferably, the DNA segment may have about 100 to 1,000 nucleotides.

The concept of anti-sense sequences is known in the art. Synthetic oligonucleotides may be prepared that are complementary to the messenger RNA encoding a target protein. The oligonucleotide or a chemically modified equivalent thereof are added to cells. The oligonucleotide binds the target mRNA and thus inhibits the translation of the target protein. (Markus-Sekura C. J., Techniques for using Anti-sense Oligonucleotides to Study Gene Expression, Analytical Biochemistry 172:289–295(1988)).

Alternatively, antisense-RNA is used to block translation of sense RNA. The antisense RNA is generated from a viral or plasmid DNA vector that contains a copy of the target gene situated in the reverse orientation with respect to the direction of transcription. A virus may be used as a carrier to introduce the inverted gene into the target cell gerome. (Izant, J. G. and Weintmub H., Science 229:345–352(1985)).

Fragments of the anti-sense DNA segment are also provided herein and they may comprise about 15 to 100 bases, and more preferably 30 to 50 bases. The anti-sense sequences may be obtained by methods known in the art such as the following.

Antisense oligonucleotides can be made by modifying their phosphate moiety to increase biological lifetime, to enhance permeability into cells and to strengthen binding to target. For example, oligomethylphosphonates (Miller, P. S., Reddy, M. P., Murakami, A., Blake, K. R., Lin, S. B. and Agris, C. H. (1986) Biochemistry 25:5092–5097), or oligophosphorothioates (LaPlanche, L. A., James, T. L., Powell, C., Wilson, W. D., Uznanski, B., Stec., W. J., Summers, M. F. and Zon, G. (1986) Nucleic Acids Res. 14:9081–9093). Alternatively, the target gene may be inserted into a viral-based eukaryotic expression vector in reverse orientation and introduced into mammalian cells (See, Sambrook, J. et al, supra).

Also part of this invention is a pharmaceutical composition which comprises a therapeutically effective amount of an anti-sense DNA sequence to the coding strand of a polynucleotide encoding a polypeptide having the antibody binding specificity of the about 70 kDalton HMFG differentiation antigen or a fragment thereof; and a pharmaceutically acceptable carrier.

The composition may be provided in different amounts. Typically, the anti-sense DNA will be provided in an amount of about 0.01 to 99.99 wt % and more preferably about 0.1 to 20 wt %, the remainder being carrier and/or other known additives. The pharmaceutically acceptable carrier may be any carrier which does not degrade DNA. Examples of carriers and other additives are buffered saline solution, human serum albumin and the like. However, others may also be utilized. The pharmaceutical composition may be prepared by admixing the anti-sense DNA with the carrier as is known in the art, freeze dried and packaged in a sterile container. The composition may be maintained refrigerated and/or frozen.

Also provided herein is a method of treating breast cancer in a subject in need of such treatment which comprises administering to the subject a composition comprising a therapeutically effective amount of an anti-sense DNA sequence to the coding strand of a polynucleotide encoding a polypeptide having the antibody binding specificity of the about 70 kDalton HMFG differentiation antigen or a fragment thereof.

This method may be practiced by administering an amount of about 5 to 800 mg anti-sense DNA, and more preferably about 20 to 200 mg anti-sense DNA in a pharmaceutical composition. The composition may be administered by a parenteral, intraveneous or intrabreast route. However, other routes of administration may also be utilized.

Part of this invention is also an immunoassay kit comprising, in separate containers a monoclonal antibody having specificity for a polypeptide provided with the antibody binding activity of the about 70 kDalton HMFG differentiation antigen; and anti-antibody immunoglobulin.

This immunoassay kit may be utilized for the practice of the various methods provided herein. The monoclonal antibody and the anti-antibody immunoglobulin may be provided in an amount of about 0.001 mg to 100 grams, and more preferably about 0.01 mg to 1 gram. The anti-antibody immunoglobulin may be a polyclonal immunoglobulin, protein A or protein G or functional fragments thereof, which may be labeled prior to use by methods known in the art.

Also provided herein is an antibody detecting kit comprising, in separate containers a polypeptide having the antibody binding specificity of the about 70 kDalton HMFG differentiation antigen; and anti-antibody immunoglobulin.

The anti-antibody immunoglobulin may be labeled prior to use.

Also provided herein is a fusion protein kit comprising, in separate containers a fusion protein comprising a polypeptide provided with the antibody binding specificity of the about 70 kDalton HMFG differentiation antigen and a second antigenic polypeptide or an antibody binding functional fragment thereof bound to one another;

an anti-second polypeptide monoclonal antibody; and anti-antibody immunoglobulin.

The fusion protein may be provided in an amount of about 0.001 mg to 100 grams in sterile form, and more preferably about 0.01 mg to 1 gram. The anti-second polypeptide monoclonal antibody may also be provided in sterile form in an amount of about 0.001 mg to 100 grams, and more preferably about 0.01 mg to 1 gram. The anti-antibody immunoglobulin may be provided in a separate container in an amount of about 0.001 mg to 100 grams and more preferably about 0.01 mg to 1 gram. The entire kit may be packaged for shipping and storage.

Also provided herein is an anti-breast cancer therapeutic kit comprising, in separate containers a monoclonal antibody having specificity for a polypeptide provided with the antibody binding specificity of the about 70 kDalton HMFG differentiation antigen; and an anti-cancer therapeutic agent selected from the group consisting of immunotoxins and radionuclides.

The monoclonal antibody is provided in an amount of about 1 to 20 grams, and more preferably about 2 to 10 grams in sterile form. The antibody may be freeze-dried and packaged. The therapeutic agent may be any known anti-cancer therapeutic agent. By means of example the agent may be abrin-A chain, ricin A-chain, immunotoxins, chemotherapy drugs and $^{131}$I and $^{90}$Y radionuclides, among others.

Having now generally described this invention, the same will be better understood by reference to certain specific examples, which are included herein for purposes of illustration only and are not intended to be limiting of the invention or any embodiment thereof, unless so specified.

EXAMPLES

Example 1

Immunoscreening of the lambda gt11 cDNA Library

A human breast cDNA library was purchased from Clontech (Palo Alto, Calif.). The library was prepared from RNA extracted from adult breast tissue excised during mastectomy, during 8th month pregnancy showing well-differentiated tissue and lactational competence. The oligo-dT primed cDNA was prepared from this tissue and then inserted into the Eco RI site of lambda/gt11.

Plating and screening of the library with monoclonal antibodies were done as described previously (Young, R. A. et al, Natl.Acad.Sci.(USA)80:1194–1198(1983)) except that a biotinylated anti-mouse antibody and horse radish peroxidase-biotin/avidin were used to visualize reactive plaques with (1 mg/ml DAB in 100 mM Tris; g/ml nickel chloride) as substrate.

Bacteriophages were plated at a density of $10^5$ pfu/150 mm plate. The library was screened with a cocktail of monoclonal antibodies Mc13 (Peterson, J. A. et al, Hybridoma (in press) 1990)) and McR2 as described previously (Ceriani, R. L. et al, Somat. Cell Genetics 9:415–427(1983)), both of which bind a about 70 Kd component of human milk fat globule (Ceriani, R. L. et al, Somat. Cell Genetics 9:415–427(1983)).

Example 2

Fusion Protein Western and Dot Blot Assays

Purified bacteriophage from positive plaques were used to lysogenize Y1089 bacteria, and lysates were prepared from IPTG induced cultures as previously described (Young, R. A. et al, Proc.Natl.Acad.Sci.(USA)22:1194–1198(1983)). The pelleted bacteria were re-suspended in 1/50 of the original volume in TBS containing 1 mm PMSF. and freeze/thawed 3 times.

The lysate was mixed 1:1 with Laemmli sample buffer (Laemmli, U.K., Nature 227:680(1970)) and 50 µl loaded per lane on a 7.5% SDS-Page gel using a Protean II mini gel/blotting apparatus (BioRad). The gel was blotted and processed according to Towbin et al, (Towbin, H., Staehelin, T., and Gordon, J., PNAS 76:4350–4354(1979)).

The filter was blocked in (TBST); containing 20% (FBS) 1 hr., incubated with primary (AB) (Mc13 at µg/ml in TBST) for 2 hrs., washed in TBST, incubated with HRP conjugated anti-mouse (promega Biotec) for 1 hr., washed and incubated with (DAB)/NiCl$_2$ for 5–10 minutes.

For dot blot analysis 10 µl of lysate or a dilution thereof was spotted directly onto nitrocellulose and allowed to air dry. The filter was then processed as the western blots.

Example 3

RNA and DNA Blot Analysis

Cell lines were grown to late logarithmic phase and total cell RNA prepared by the method of Chirgwin et al, (Chirgwin, J. M. et al, Biochemistry 18:5294–5299(1979). Genomic DNA was precipitated from guanidinium isothyocyanate lysates by adding 2 volumes ethanol and purified as previously described (Sambrook, et al, in Molecular Cloning: A Laboratory Manual, Second Edition, Cold Spring Harbor Press, N.Y. (1989)).

RNA was glyoxalated, electrophoresed, and blotted according to Thomas (Thomas, P., Proc.Natl.Acad.Sci.(USA)77:5201–5205(1980)) except that blots were done on Duralose-UV (Stratagene) and RNA bound to the filter using UV irradiation. DNA blots were similarly treated and processed according to Southern (Southern, E., Academic Press 68:152–176(1979)).

Radiolabeled cDNA insert probes were prepared using the random priming method (Feinberg, A. P. et al, Anal.Biochem.132:6–13(1983)) and 32 [P] dATP (Amersham). Single stranded RNA probes were made in vitro, using SP6 or T7 RNA polymerase according to the specification of the manufacturer (Promega Biotec) and labelled by incorporation of [$^{32}$P] UTP (Amersham).

The hybridization of RNA probes to RNA blots was conducted at 65° C. and to DNA blots at 50° C. in 50% formamide. The highest stringency wash was at 65° C. 0.1×SSC (0.1% SDS), except for some RNA probes which gave high background.

RNAs treatment (1 µg/ml for 1 hrs. in (2×SSC)) was followed by 0.5 hrs. at 50° C. 0.1×55c. 0.1% SDS was used to remove non-specific hybridization to ribosomal RNA. The blots were exposed to X-ray film (Kodak X-AR) at 80° C. with intensifying screens.

Example 4

DNA Sequencing

Large scale bacteriophage DNA preparations were made from phage lysates, and the Eco R1 digested cDNA insert subcloned into pGEM3 according to standard protocol (Sambrook, et al, in Molecular Cloning: A Laboratory Manual, Second Edition, Cold Spring Harbor Press, N.Y. (1989)). Dideoxy sequencing of the insert in pGEM3 was done using a modified T7 DNA polymerase (sequenase) directly on the plasmid DNA using T7 or SP6 promoter sequence primers (Promega Biotec) according to the manufacturer's protocol (USB).

Example 5

Isolation and Characterization of cDNA Clones Encoding Mc13/McR2 Antigen

A cocktail of Mc13 and McR2 was used to screen a lambda/gt11 cDNA library from human lactating breast tissue (Clontech). Out of 900,000 phage screened, 3 were found positive through repeated rounds of plaque purification. One of these, BA 70.1, bound to both Mc13 and McR2, while the other two bound Mc13 weakly and not at all to McR2. BA 70.1 was therefore characterized further. The results obtained are shown in Table 1 below.

TABLE 1

Screening of Lamda/gt[11] Library

|  | Mc1 | Mc5 | Bre1 | Bre3 | DF3 | McR2 | Mc13 | Mc3 | Mc3 | Mc15 | Mc16 |
|---|---|---|---|---|---|---|---|---|---|---|---|
| BA 70.1 | − | − | − | − | − | + | + | − | − | − | − |
| BA 70.2 | − | − | − | − | − | − | + | − | − | − | − |
| Mucin Synthetic 20 aa Repeat | + | + | + | + | + | − | − | − | − | ND | ND |
| lambda/gt11 | − | − | − | − | − | − | − | − | − | − | − |

ND = Not Done

As shown in Table 1, the fusion protein made by Y1089 cells lysogenized with BA 70.1 only binds anti 70 kDalton component antibodies and not the six different NPGP antibodies or the four different 46 kDalton component antibodies. Mc13 and McR2 did not bind control lambda Y1089 lysates.

Figure 1:
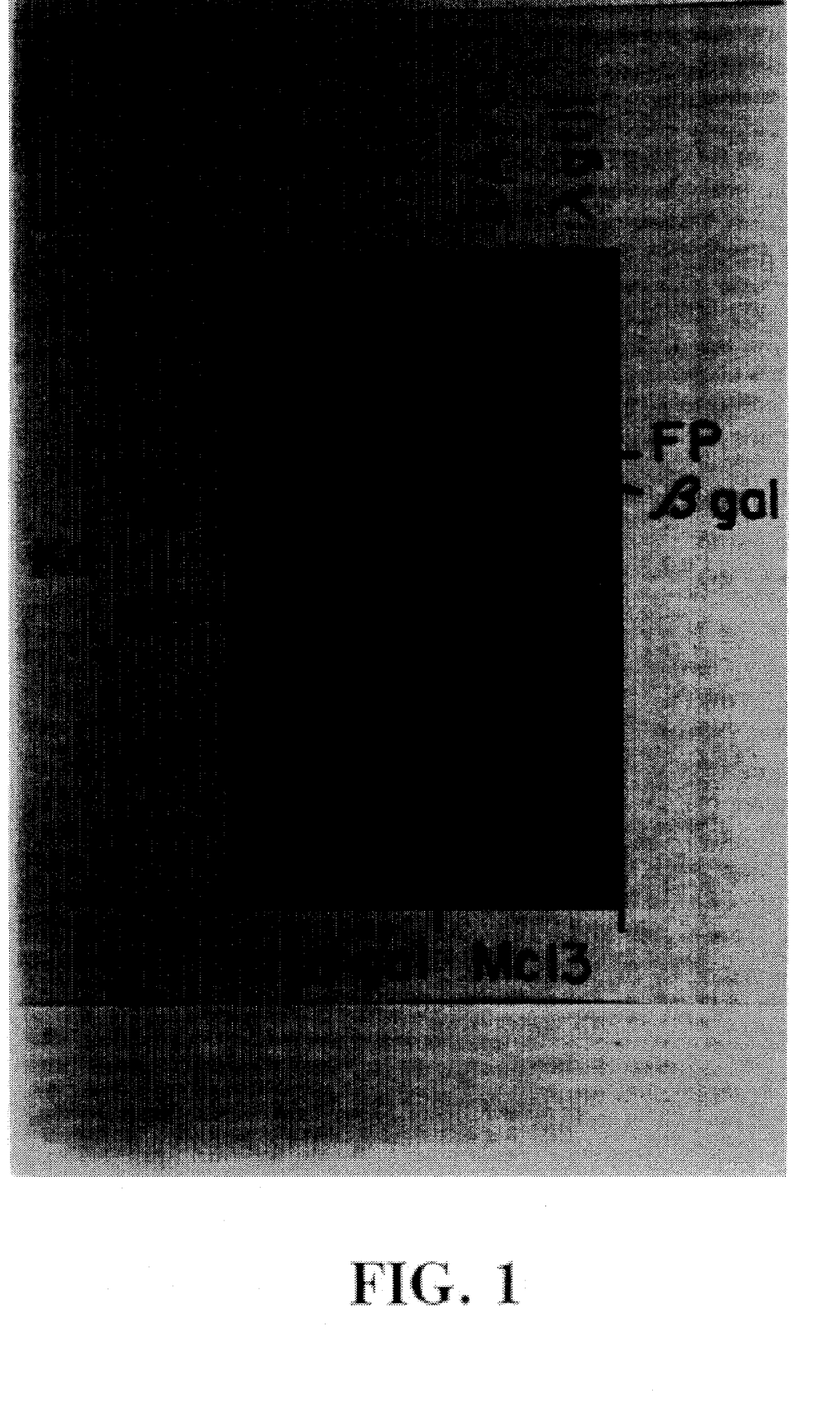
FIG. 1 is an immunoblot of the BA 70.1/βgal fusion protein. Protein extracts from BA 70.1 and lambda/gtll lysogens were prepared and run on 10% polyacrylamide gel electrophoresis (PAGE), blotted on nitrocellulose, and processed with anti-βgal antibody (lanes 1 and 2) or monoclonal antibody Mc13 (lanes 3 and 4). A BA 70.1 extract is shown on lanes 1 and 3; a lambda/gtll extract is shown in lanes 2 and 4. FP stands for fusion protein. The size markers are pre-stained high molecular weight markers from BRL (in kilodaltons).

The BA 70.1/β-gal fusion protein was further analyzed by western blotting. As shown in FIG. 1, this indicates that the fusion protein is about 11 kDaltons larger than the β-galactosidase made by lambda. Fusion proteins made by the two other positive phages were about the same size as β-galactosidase indicating the presence of stop codons within the insert of at least BA 70.2. The size of the insert from this latter cDNA clone is approximately 800 base pairs (bp).

Example 6

Sequence of BA 70.1 cDNA

The sequence of the BA 70.1 cDNA and its deduced amino acid sequence are shown in Table 2 below.

TABLE 2 cDNA and Aminoacid Sequence of BA 70.1 Fragment

```
         10                  20                  30                  40                  50
CGG TCC AAA TGG AGT GAG AGA ACA AGA AAG CCT CTA GAA GCC CTC TAT GGG
Arg Ser Lys Trp Ser Glu Arg Thr Arg Lys Pro Leu Glu Ala Leu Tyr Gly 60                  70                  80                  90                 100
TAT GAC TAC TTT GCC AGA ACC TGT GAA AAG TGG GTG GAT GGC ATA AGA CAG
Tyr Asp Tyr Phe Ala Arg Thr Cys Glu Lys Trp Val Asp Gly Ile Arg Gln 110                 120                 130                 140                 150
TTT AAA CAT CTC CCA GAT GGT AAC ATC TGC CGG CAC CTG CTG CCC CGG GTC
Phe Lys His Leu Pro Asp Gly Asn Ile Cys Arg His Leu Leu Pro Arg Val 160                 170                 180                 190                 200
CAG TGC CCC GCC TTG ATT GTG CAC GGT GAG AAG GAT CCT CTG GTC CCA CGG
Gln Cys Pro Ala Leu Ile Val His Gly Glu Lys Asp Pro Leu Val Pro Arg 210                 220                 230                 240                 250
TTT CAT GCC GAC TTC ATT CAT AAG CAC GTG AAA GCG TCA CGG CTG CAT TTG
Phe His Ala Asp Phe Ile His Lys His Val Lys Ala Ser Arg Leu His Leu 260                 270                 280                 290
ATG CCA GAA GGC AAA CAC AAC CTG CAT TTG CGT TTT GCA GAT
MET Pro Glu Gly Lys His Asn Leu His Leu Arg Phe Ala Asp
```

This sequence only has one uninterrupted open reading frame (ORF) extending the length of the EcoR1 insert (297 bp). No extended identity was found when this 99 amino acid sequence was compared to the swiss-pro database (PFSTSCN; PCGENE).

The cDNA sequence shown, in addition, did not have extended identity with any sequences in GENBANK (FASTA; Intellegenetics Suite). However, when a direct matrix comparison was made between the BA 70.1 sequence and the mucin sequence reported by Taylor-Papadimitriou (Gendler, S. et al, Biological Chemistry 263:12820–12823(1988)) a short sequence (14 bp) had 93% identity. This is shown in Table 3.

TABLE 3

Comparison of BA 70.1 and PEM Core sequences*

```
PEM Core  56                       69
              GT—C A A A T G G A A T G A
              | |   | | | | | | | | | | | |
BA 70.1       G T C C A A A T G G A G T G A
              3                          17
```

*Gendler, S. et al, J. of Biological Chemistry 262: 2820-12823(1988).

Example 7

Structure of BA 70.1 Gene in Human Breast Cells

Genomic DNA was isolated from several human breast cell lines and lymphoid cells (Raji), digested with Eco R1 and Hind III, blotted and hybridized to labeled BA 70.1 probe. Analysis of the BA 70.1 gene by Southern blot showed several restriction fragment length polymorphisms (RFLP) among 6 human cell lines (See, FIG. 3). The BA 70.1 cDNA detected 2 Eco R1 fragments in MDA361 and Raji genomic DNA, a doublet at about 10.0 kb. However, only the smaller fragment was detected in E11-G, HS578T and MCF7 cell DNA while only the larger band was seen in ZR75 cell DNA.

Figure 3A:
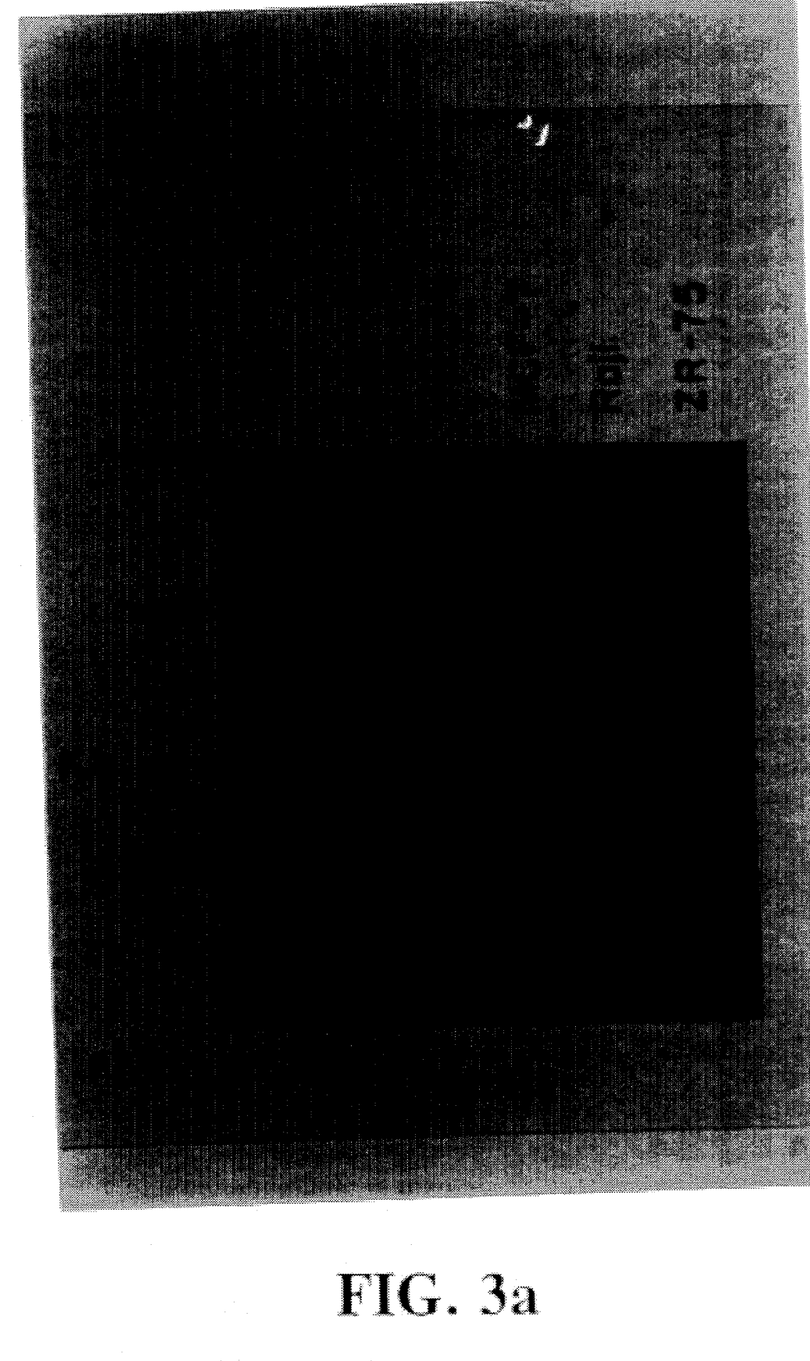
FIG. 3 shows a DNA blot analysis of restriction enzyme digested human cell line DNA, cut with EcoR1 (A) or Hind III (B). The blots were probed with BA 70.1 $^{32}$p RNA as in FIG. 2. Approximately equal amounts (10 μg) of total cell DNA were loaded in each lane except for ZR75 DNA which had about one half as much DNA as confirmed by ethidium bromide staining. Molecular weight size standards from Hind III digested lambda DNA are shown on left side.
Figure 3B:
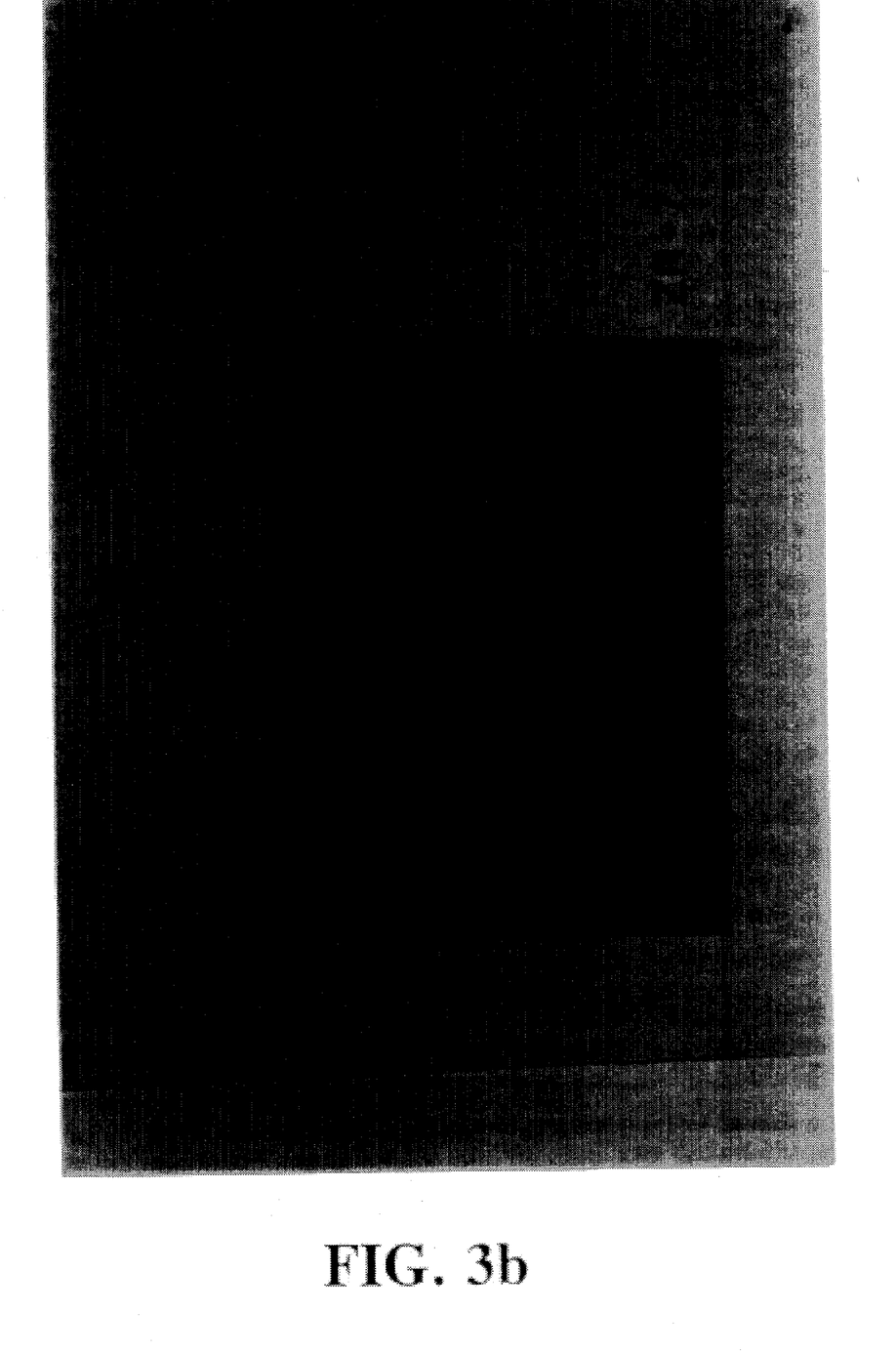

Three Hind III fragments were detected in MDA361 and MCF7 DNA that were about 9.2 kb, 8.6 kb and 6.7 kb. long. Only the about 8.6 kb and 6.7 kb long Hind III fragments were detected in HS578T and Raji DNA and only the 6.7 kb and 9.2 kb long Hind III fragments were found in ZR75 DNA. Similar polymorphisms were seen with BamH1 digested cell line DNAs but not with PstI or XbaI digested DNA (data not shown).

The relative intensities of these bands vary among the cell lines perhaps because of chromosome loss and heterogeneity within a cell line. The pattern of restriction fragment bands detected in these cell lines with the BA 70.1 probe is clearly distinct from the Hind III and EcoR1 patterns previously observed with the breast mucin probe in the same cell lines. (Gendler, S. J. et al, Proc.Natl.Acad 85:2320–2323(1988); Siddiqui, J. et al, Proc.Natl.Acad.Sci.85:2320–2323(1988); Gendler, S. et al, Biological Chemistry 263:12820–12823(1988)).

Example 8

Expression of the BA 70.1 Gene in Human Breast and Other Cell Lines

Figure 2:
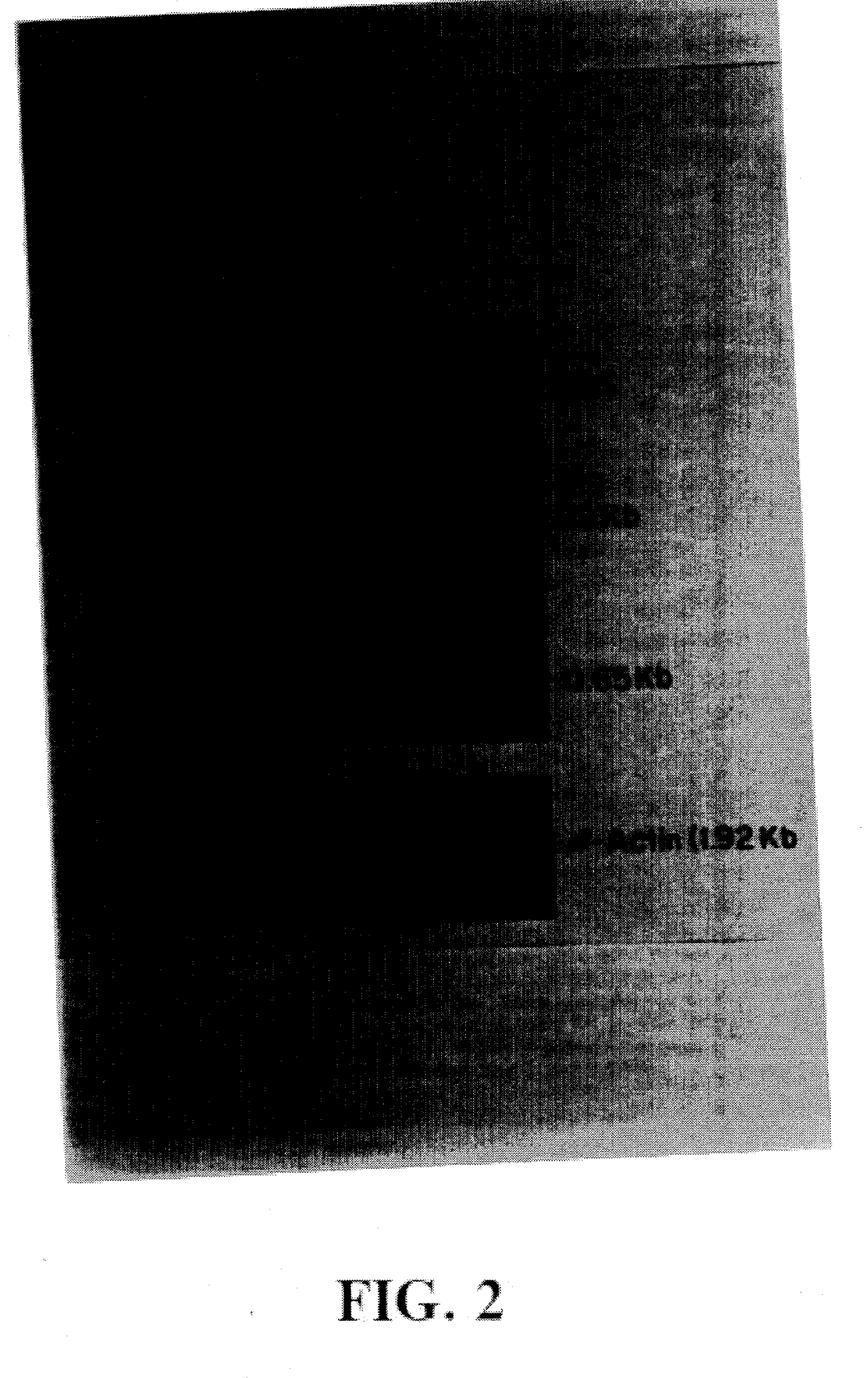
FIG. 2 shows RNA blot analysis of human cell line total RNA probed with $^{32}$p labeled BA 70.1 single stranded RNA (complement of sequence shown in Table 2). 10 μg of each RNA were loaded per lane. The RNA probe was removed from the blot by incubation at 100° C. in distilled water for 15 minutes, and the blot rehybridized to a $^{32}$p radiolabelled 24 base actin oligonucleotide probe (Clontech, Palo Alto, Calif.). The resulting 1.9 kb band is indicated.

A single stranded RNA probe complementary to the coding strand of BA 70.1 was used to probe RNA blots of total RNA from various human cell lines. The results are shown in FIG. 2 and Table 4 below.

TABLE 4

Expression of BA 70.1 Specific mRNA in Human Tumor Cell Lines

| Cell Line | 1.8 kb RNA | 0.65 kb RNA |
|---|---|---|
| MDA-MB-361 (breast) | ++ | + |
| MDA-MB-331 (breast) | ++ | + |
| MCF7 (breast) | ++ | + |
| T47D (breast) | ++ | + |
| ZR75 (breast) | ++ | + |
| BT20 (breast) | + | + |
| SKBR3 (breast) | + | + |
| E11-G (breast) | + | + |
| HS578T (breast) | ++ | + |
| HeLa (Cervix) | ++ | + |
| HT29 (Colon) | ++ | + |
| Pan Cl (Pancreas) | +++ | + |
| SKOV3 (Ovary) | ++ | + |
| A549 (Lung) | ++ | + |
| Raji (B cell) | + | + |

A 1.8 kbase RNA was detected that was highly expressed in all human breast cell lines assayed compared to relatively low levels in Raji cells. A second smaller RNA (0.65 kbase) was also detected which appeared to accumulate at about the same levels in all cell lines assays.

The same blots were probed with a labeled coding RNA strand which showed no specific bands above background.

The invention now being fully described, it will be apparent to one of ordinary skill in the art that many changes and modifications can be made thereto without departing from the spirit or scope of the invention as set forth herein.

We claim:

1. An isolated pure polydeoxyribonucleotide consisting of a DNA segment encoding the component of the human milk fat globule (HMFG) which comprises the amino acid sequence of Table 2, the apparent molecular weight of the HMFG component being determined by denaturing gel electrophoresis.

2. The polydeoxyribonucleotide of claim 1, wherein the DNA segment is that shown in Table 2.

3. An isolated, pure polydeoxyribonucleotide, comprising a DNA segment which is complementary to the coding strand of the polydeoxyribonucleotide of claim 1.

4. The polydeoxyribonucleotide of claim 1, wherein the encoded component consists of the 70 Kd apparent molecular weight human milk fat globule antigen, as determined by denaturing gel electrophoresis.

5. The polydeoxyribonucleotide of claim 1 in labeled form.

6. A composition, comprising the polydeoxyribonucleotide of claim 1; and an inert, non-hydrolytic carrier.

7. A pure, isolated polyribonucleotide consisting of an RNA segment that hybridizes under stringent conditions to the polydeoxyribonucleotide of claim 1.

8. The polyribonucleotide of claim 7, in labeled form.

9. An isolated, pure polyribonucleotide, consisting of an RNA sequence that is complementary to the polydeoxyribonucleotide of claim 1.

10. A composition, comprising the polyribonucleotide of claim 7; and an inert, non-hydrolytic carrier.

11. A polydeoxyribonucleotide encoding a fusion protein, the polydeoxyribonucleotide comprising the polydeoxyribonucleotide of claim 1; and a second polydeoxyribonucleotide bound thereto encoding a further polypeptide.

12. A composition, comprising the polydeoxyribonucleotide of claim 11; and an inert, non-hydrolytic carrier.

13. A polyribonucleotide encoding a fusion protein, comprising the polyribonucleotide of claim 7; and a second polyribonucleotide bound thereto encoding a further polypeptide.

14. A composition, comprising the polyribonucleotide of claim 13; and an inert, non-hydrolytic carrier.

15. A hybrid vector comprising a vector having operatively linked in reading frame thereto the polydeoxyribonucleotide of claim 1.

16. A transfected host cell comprising a host cell carrying the hybrid vector of claim 15.

17. A hybrid vector comprising a vector and operatively linked thereto the polydeoxyribonucleotide of claim 11.

18. A transfected host cell comprising a host cell carrying the hybrid vector of claim 17.

19. A method of expressing a polypeptide, comprising obtaining the host cell of claim 16;

culturing the transfected host cell in an expression medium; and allowing the expression of the polypeptide to occur.

20. A method of obtaining a purified polypeptide, comprising the method of claim 19; and separating the polypeptide from the medium and the cells.

21. A method of obtaining a purified fusion protein, comprising the method of claim 20; and separating the fusion protein from the medium and the cells.

22. A fusion protein obtained by the method of claim 21.

* * * * *